(12) United States Patent
Wong, Jr. et al.

(10) Patent No.: US 7,229,468 B2
(45) Date of Patent: Jun. 12, 2007

(54) MEDICAL DEVICE AND METHOD FOR TEMPERATURE CONTROL AND TREATMENT OF THE EYE AND SURROUNDING TISSUES

(76) Inventors: Edward K. Wong, Jr., 23 St. Tropez, Newport Beach, CA (US) 92660; Timothy L. Lee, 2796 Milo Hae Loop, Koloa, HI (US) 96756; Markus D. Wong, 23 St. Tropez, Newport Beach, CA (US) 92660

( * ) Notice: Subject to any disclaimer, the term of this patent is extended or adjusted under 35 U.S.C. 154(b) by 0 days.

(21) Appl. No.: 11/285,690

(22) Filed: Nov. 22, 2005

(65) Prior Publication Data
US 2006/0136022 A1   Jun. 22, 2006

Related U.S. Application Data

(60) Provisional application No. 60/630,806, filed on Nov. 23, 2005.

(51) Int. Cl.
*A61F 7/00* (2006.01)
(52) U.S. Cl. ........................ 607/104; 607/109
(58) Field of Classification Search .............. 607/96, 607/104, 108, 109; 601/159, 160
See application file for complete search history.

(56) References Cited

U.S. PATENT DOCUMENTS

| | | | | |
|---|---|---|---|---|
| 4,108,146 A | * | 8/1978 | Golden | 607/104 |
| 4,387,707 A | * | 6/1983 | Polikoff | 601/37 |
| 6,024,095 A | * | 2/2000 | Stanley, III | 128/898 |
| 6,406,447 B1 | * | 6/2002 | Thrash et al. | 601/160 |
| 6,908,195 B2 | * | 6/2005 | Fuller | 351/158 |
| 6,918,904 B1 | * | 7/2005 | Peyman | 606/5 |

* cited by examiner

*Primary Examiner*—Roy D. Gibson
(74) *Attorney, Agent, or Firm*—Walter A. Hackler

(57) ABSTRACT

The invention provides a medical device having a thermister for temperature measurement, irrigation/aspiration ports for fluid exchange and application of therapeutic modalities, a pressure manometer for pressure measurement, and an external system for control of temperature, pressure, and flow rate. When applied to the eye and orbit, this device can be used in hypothermia or hyperthermia applications, the control of intraocular pressure (IOP), and the application of treatment modalities. Methods of using the device in treating patients suffering from central retinal artery occlusion, anterior optic nerve disease, pathology of the choroid and retina including the macula, inflammation of the eye including the vitreous and anterior segment, glaucoma, inflammation and/or infections of the anterior and/or posterior segment of the eye, treatment before/during/after surgery of the eye, and the application of treatment modalities through a semi-permeable membrane are described.

24 Claims, 13 Drawing Sheets

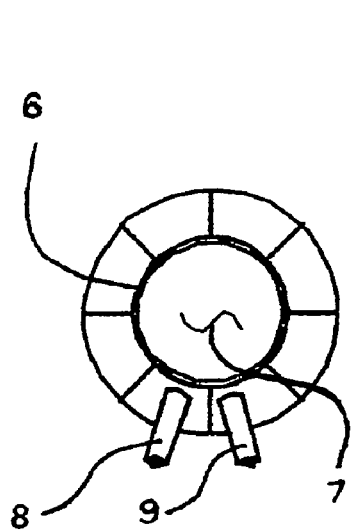
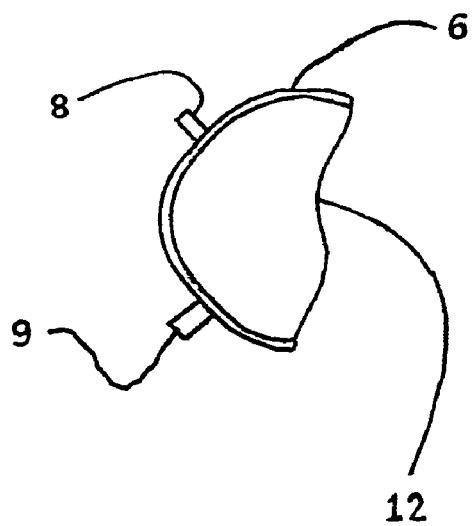
Fig 2  Fig 3
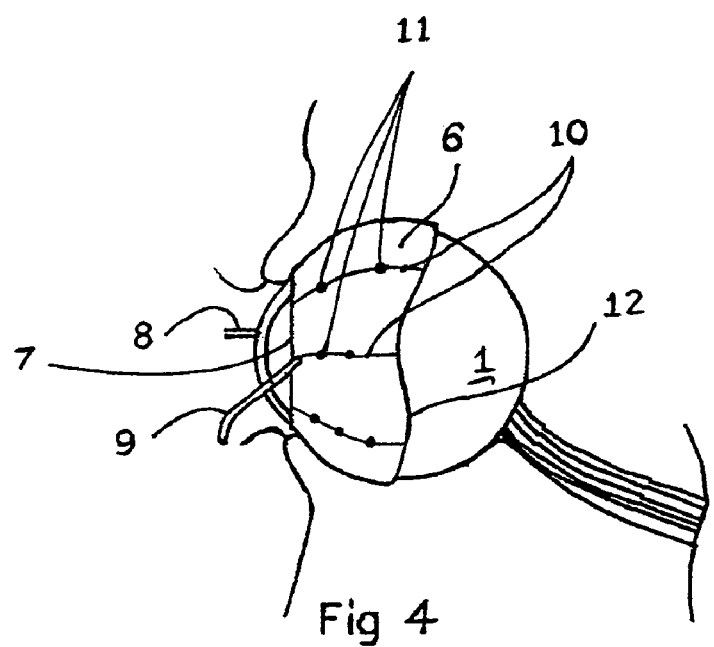
Fig 4

MEDICAL DEVICE AND METHOD FOR TEMPERATURE CONTROL AND TREATMENT OF THE EYE AND SURROUNDING TISSUES

The present application claims priority of U.S. Ser. No. 60/630,806 filed Nov. 23, 2005 which is incorporated herewith in its entirety.

FIELD OF THE INVENTION

The present invention generally relates to medical devices useful in reducing and preventing injury to the eye and orbit by inducing local temperature control of the tissue and by administering a constant source of medication(s). More specifically, the invention provides devices for surrounding the exterior surface of the eye for use in hypothermia or hyperthermia applications, the rapid flow of fluid using conduction and convection principles, the application of treatment modalities, and the transmission of temperature control to other tissues of the orbit including the adnexae, the optic nerve, and extra-ocular muscles. The medical device has a thermister for temperature measurement, irrigation/aspiration ports for fluid exchange and application of therapeutic modalities, and a flexible inflatable unit that surrounds the external surface of the eye. An external system for control of temperature, pressure and flow rate is described.

BACKGROUND OF THE INVENTION

Lack of blood flow (ischemia) to the eye may result in death of the tissues in the optic nerve and retina/choroid. In the case of central retinal artery occlusion (CRAO), there is a particle (embolus) in the major blood vessel giving oxygen and nutrients to the retina. In the case of anterior ischemic optic neuropathy (AION), there may be an occlusion of the blood vessel (s) entering the eye in the anterior optic nerve. With optic neuritis (ON) involving the anterior optic nerve, there is an inflammation of the optic nerve due to disease in the myelin sheath, the covering of the nerve fibers that exit the eye. After a period of time (minutes to hours to days), death of the tissue may occur causing irreversible damage.

Pathology to tissues of the eye may occur due to blunt injuries, such as a blow to the eye/orbit, resulting in hemorrhage within or around the eye and associated swelling of eye tissue. Unfortunately, it is often difficult to control injury to the eye using conventional ophthalmological means including medical and surgical intervention.

Various other diseases of the eye and the orbit may result in swelling of tissue with consequent loss of function. Inflammation of orbital tissue is usually managed with systemic medical therapy or even surgical decompression. Other types of inflammation of the tissues within the eye include posterior uveitis, choroiditis, retinitis, vitritis, scleritis, thyroid-related eye disease, phacoanaphylaxis, anterior uveitis, and sympathetic ophthalmia. Secondary glaucoma may result from inflammation involving the anterior segment of the eye.

Infections of the eye may involve the cornea, the sclera, the vitreous, the retina/choroid, the ciliary body, the lens, and the anterior chamber. They are usually treated with systemic antibiotics, sometimes systemic steroids, and topical drops of antibiotics, and intraocular antibiotic injections.

Current treatment for swelling or inflammation of the eye and orbit is not always satisfactory. In the severely injured eye or orbit, medical therapy to control swelling is usually applied systemically resulting in high levels of medication in the rest of the body with very low concentrations reaching the eye or orbit. Surgical intervention to decompress the eye and/or orbit requires major intervention through opening the bony walls of the orbit or skull to expose the area and prevent compression against the fixed volume of the bony walls. In the case of severe swelling of the sheath around the optic nerve, surgical decompression of the sheath has been attempted in severe cases of papilledema, anterior ischemic optic neuropathy, and severe trauma. The results have variable reports of success and failure of the procedures.

Hypothermia has proved encouraging in the recent literature for the purpose of decreasing oxygen consumption and for decreasing swelling of the brain and other central nervous system (CNS) tissue. Since the eye is part of the CNS, it seems logical that hypothermia of the eye may decrease swelling of the eye and optic nerve in the same way as hypothermia of the brain prevents brain swelling. Unfortunately, cooling of the entire body to cool the brain does have inherent dangers, and similarly cooling of the eye by cooling the body may also have deleterious effects. The heart responds to hypothermia with arrhythmias, and the blood clotting mechanisms may be severely impaired resulting in hemorrhage. Moreover, cooling the body only results in a few degrees of cooling of the CNS. In the case of the eye, attempts have been made to cool the vitreous of the eye during retinal and vitreous surgery by surgically entering the eye and cooling it from within. A recent animal study on viability of CNS tissue of the eye after hypothermia demonstrated similar preservation of function.

With the new technologies now available, it is time for a new approach to controlling the temperature of the CNS and the eye and orbit by doing local cooling from outside surface of the eye without entering the eye surgically. By administering medications to the eye/orbit directly in a continuous fashion coupled with hypothermia, there may be a new approach to treating eye disease.

SUMMARY OF THE INVENTION

The invention provides devices and methods for enhancing the treatment of diseases of the eye and orbital tissues. More specifically, the invention provides devices and methods for controlling the temperature of the eye, optic nerve, orbit, and peri-orbital tissues by applying hypothermia, hyperthermia, or euthermia rapidly without violating the tissue with surgical intervention. Moreover, the devices and methods can also apply medications and/or chemicals to the eye, optic nerve, orbit, and peri-orbital tissues.

The first embodiment of the device comprises a thermal-regulating shell consisting of a multi-layered spherical unit that conforms to the shape of the eye, fitting into the fornices of both the upper and the lower eyelids. Fluid will flow into an entry port and out through the exit port. Rapid flow of fluid will result in both convection and conduction exchange of temperature between the device and the surrounding tissues, including the eye and its adnexae. Rapid flow of fluid will facilitate the administration of appropriate medications and/or chemicals to the adjacent tissues through a semi-permeable membrane, or nanotubules, or millipore/micropore system, or other appropriate materials that deliver treatment to the tissues. In diseases such as central retinal artery occlusion, it is desirable to rapidly lower the temperature within the neurological tissue of the eye to preserve it from ischemic injury. In other diseases such as uveitis, ocular infection, and ocular inflammation a slower flow of fluid may be efficacious.

A pump system may be configured with a peristaltic pump with multiple inlet and outlet connections that have the capability of transporting large volumes of fluid rapidly throughout the entire volume of the thermal-regulating shell, distributing the fluid through channels within the shell. Depending upon flow characteristics, the system may be custom designed for the best delivery of fluid to the tissues of the eye, the orbit, and adjacent sinuses and other periorbita. The pump may be battery operated and simplified to allow for portability and ease of use. An external system will control temperature, pressure and flow rate.

The thermal-regulating shell may be designed with an opening in front of the cornea to allow for measurement of intraocular pressure and for viewing the structures within the eye from the cornea to the retina and optic nerve. If the shell is designed without the opening in front of the cornea, then thermoregulation and administration of therapeutics to the anterior segment of the eye may be facilitated.

In order to place the shell around the eye and beneath the eyelids, an inserter will allow for gentle placement of the thermal-regulating shell beneath the lids. The shell will be designed with a semi-firm material such as metal or plastic or other synthetic substance placed into the shell to give shape and firmness. This may be configured in a ribbing pattern or a matrix to keep the shell in contact with the surface of the eye. Once the shell is in position, the inserter is removed, and the shell remains in close contact to the eye.

When treating the posterior orbita including the optic nerve, it may be desirable to surgically open the superior and/or inferior fornices to allow the thermo-regulating shell to enter the orbit more posteriorly, closer to the tissue to be treated.

In the case of central retinal artery occlusion, it may be advantageous to create pulsations with both positive and negative pressure through the dual-layered shell. The pulsations of the shell will generate differential pressures within the eye, allowing for dispersion of the embolus out of the major retinal artery. Eye-pressure measuring devices can be built into the shell to monitor intraocular pressure and regulate the fluids flowing through the shell to prevent excessive pressure on the eye.

By coating the outer surface of the shell with an insulating material such as a ceramic, direction of thermal regulation and delivery of medications can be targeted more toward the eye. By coating the inner surface of the shell with appropriate films, one may direct thermal regulation and delivery of medications to other tissues of the orbit, periorbita, and surrounding sinuses.

Medications may more easily penetrate the sclera of the eye resulting in higher levels within the eye. Since the shell will be placed behind the equator of the eye, therapy will be directed into the posterior half of the eye including the vitreous, the retina, the choroid, the macula, and the anterior optic nerve. Temperature control will also extend to the posterior half of the eye. In the case of hypothermia, preservation of the neurological tissue of the retina and optic nerve can be achieved despite insult such as ischemia. The physician will have a longer period of time to treat the insult with medical therapy and/or surgery.

In the case of infections of the anterior segment of the eye, hypothermia and appropriate medical therapy will both halt the progression and destroy the infective agent. Infections within the eye (endophthalmitis) will also respond to hypothermia and appropriate medical therapy, especially with rapid cooling and constant administration of appropriate medical therapy into the eye through the sclera. Rather than giving large doses of systemic antibiotics or other anti-infectious agents, it may be possible to produce effective levels of medication by delivering therapy closer to the site of infection.

Inflammation of the eye will respond to both hypothermia and appropriate medical therapy. This includes diseases such as anterior and posterior uveitis, retinitis, choroiditis, vasculitis, papillitis, sympathetic ophthalmia, scleritis, episcleritis, vitritis, and other diseases. Since the entire eye can be cooled rapidly, these diseases can be better controlled without damage to the eye.

Inflammation of the orbit, ocular adnexae, and ocular muscles can be better managed by utilizing hypothermia in conjunction with appropriate anti-inflammatory medications such as steroids, non-steroidal anti-inflammatory drugs, and antimetabolites. Such inflammatory diseases may include Graves' eye disease with exophthalmous and pseudotumor of the orbit.

Infections of the orbit may be amenable to hypothermia and appropriate medical therapy. Shielding the eye from such therapy may be accomplished by coating the surface of the shell that abuts the eye with an insulator such as a ceramic compound. In this way, therapy can be directed away from the eye, toward the infection in the orbit.

Tumors of the eye may be amenable to both hypothermia and hyperthermia. Hypothermia may be an adjunct to pre-surgical treatment, surgical therapy, and post-operative management. Hyperthermia may be helpful in augmenting the effect of laser therapy, photodynamic therapy, and medical therapy.

Macular disease may respond to a combination of medical therapy, laser therapy, and hypothermia. Preservation of retinal tissue and the prevention of edema of the macula before and/or after laser therapy may be accomplished with this system of thermal control and drug delivery.

In patients who have surgery on the back or neck, they are in a prone position resulting in congestion of the orbit, poor venous drainage, and occasionally blindness. A new approach to prevention of ischemic optic neuropathy following such surgical intervention can be accomplished by using a method of pumping tissue fluid and venous drainage from the orbit to the cavernous sinus.

BRIEF DESCRIPTION OF DRAWINGS

FIG. 2: Represents a frontal view of a thermal regulating shell with entry and exit ports when it is positioned onto the eye;

FIG. 3: Depicts the side view of the thermal-regulating shell when conformed to the shape of the eye;

FIG. 4: Displays the side view of the shell placed over the surface of the eye, beneath the lids, and into the upper and lower fornices, a meshwork may be used for structural support and for connecting sensing devices to the eye;

DETAILED DESCRIPTION

Figure 1:
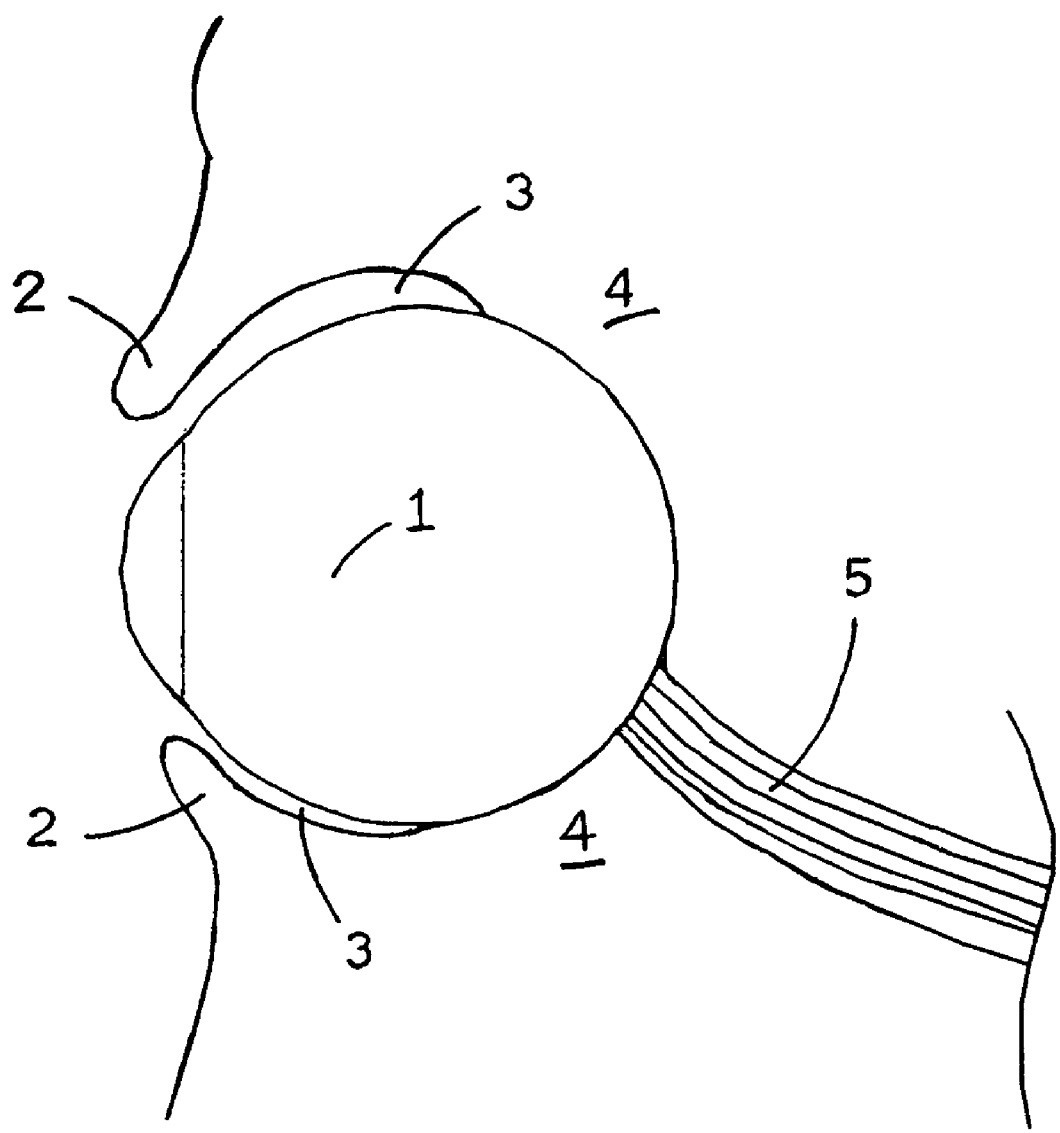
FIG. 1: Represents a side view of the eye, eyelids, optic nerve, and upper and lower formices.
Figure 5:
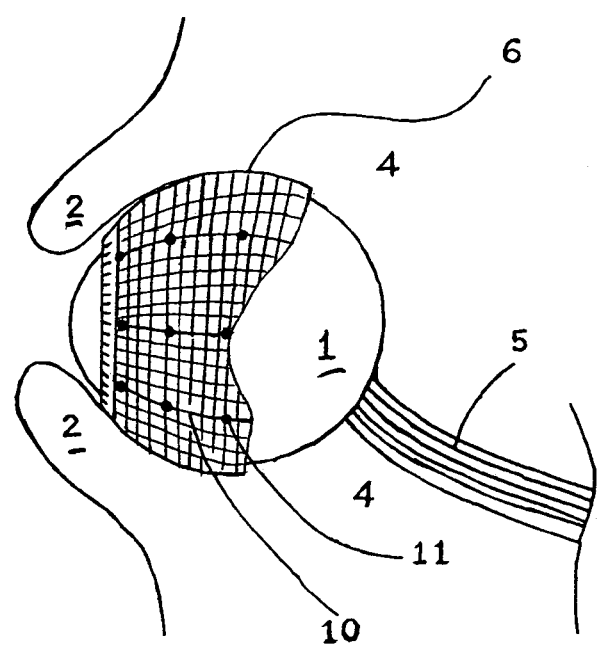
FIG. 5: Displays the side view of the shell over the surface of the eye with the integration of a wire-mesh structure onto the shell for support and embedded sensors for data collections points, and stereotatic coordinates for localization of instrumentation and placement of drug delivery, radiation or other treatment means.

In FIG. 1, the normal anatomy is shown of a side view of an eye 1, with upper and lower eyelids 2, upper and lower fornices 3, orbit 4 and optic nerve 5.

A thermal-regulating shell 6 in accordance with the present invention is illustrated in FIG. 2 (front view) and FIG. 3 (side view). As seen in FIG. 3 the cross-sectional view of the thermal-regulating shell 6 supports a posterior opening 12 suitable in size to allow the shell 6 to conform and slip over the eye 1.

FIG. 4 shows the general position of the device 6 when positioned onto the eye 1. The thermal-regulating shell 6 comprises a fluid cavity suitably designed to facilitate temperature controlled fluid to be circulated within the thermal-regulating shell 6.

The thermal-regulating shell 6 may include a suitably designed central anterior opening 7, a fluid entry port 8, and a fluid exit port 9, both in fluid communication with the shell 6. Other structures such as wires 10 or other suitable semi-rigid means, seen most clearly in FIG. 4, may be incorporated into the thermal-regulating shell 6 which can facilitate fluid flow within the shell 6. This provides a supporting structure as well as a method to direct fluid evenly or preferentially for improved thermal transfer between the eye 1 to the thermal regulating shell 6.

Figure 6:
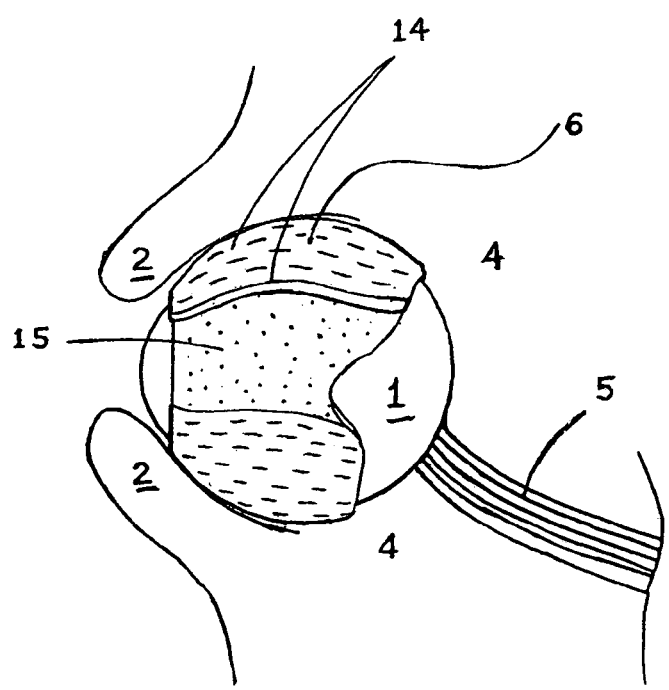
FIG. 6: Represents the side view of the shell with the shell lumen partially inner system exposed, where a substance such as a medicament can be administered to the eye through its semi-permeable inner shell membrane or to the orbital tissue through its semi-permeable outer shell membrane and its peripheral tissues.

In FIG. 6, medicament or other fluids will pass through its semi-permeable membrane to the eye 1 and/or surrounding orbital 4 tissues. Microtubules 13, nanotubules, micropores or other transport system will deliver this medicament through its inner semi-permeable membrane 15 and/or outer semi-permeable 14 layer.

Figure 7:
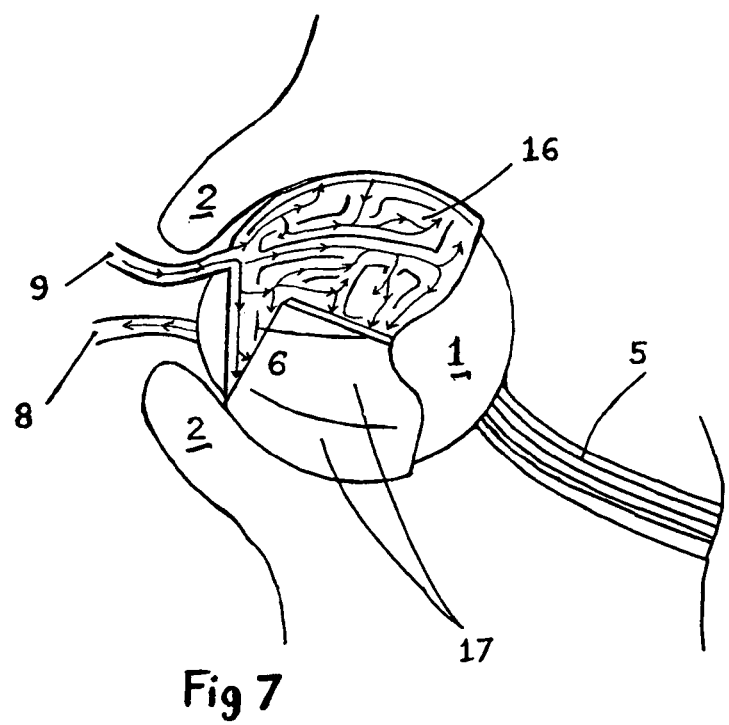
FIG. 7: Displays the side view of the shell with the shell lumen partially exposed, showing the inner fluid channels and cavities exposed below its outer layer.
Figure 8:
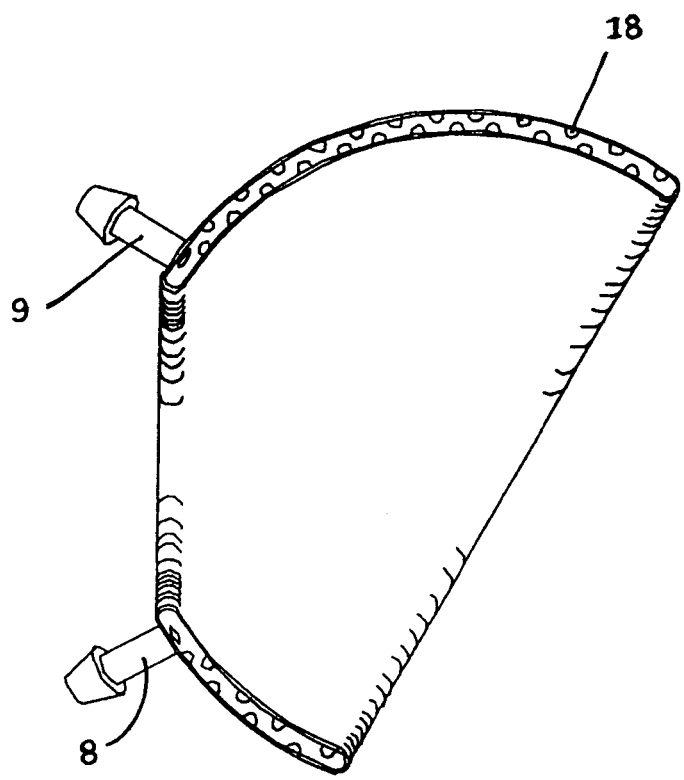
FIG. 8: Depicts the sectional view of the shell with its channels and ridges within the shell lumen.

Within the inner system of the shell in FIG. 7, there are cavities 17 where fluid flows through its channels 16 to optimize thermal transmission. This system of channels and cavities throughout the shell are shown in FIG. 7 side view and FIG. 10's section view. The channels are formed by ridges 18 best seen in FIG. 8.

Figure 9:
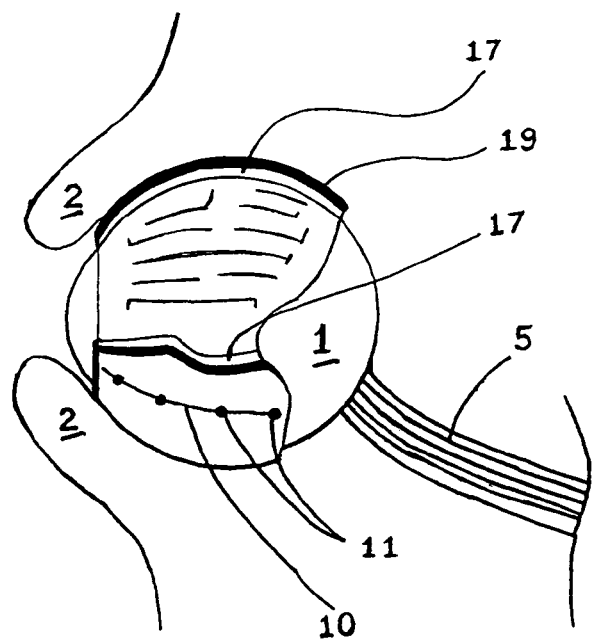
FIG. 9: Provides a side view of the plural layer shell with a more rigid structure such as ceramic insulation or lead shielding on its outer layer.
Figure 10:
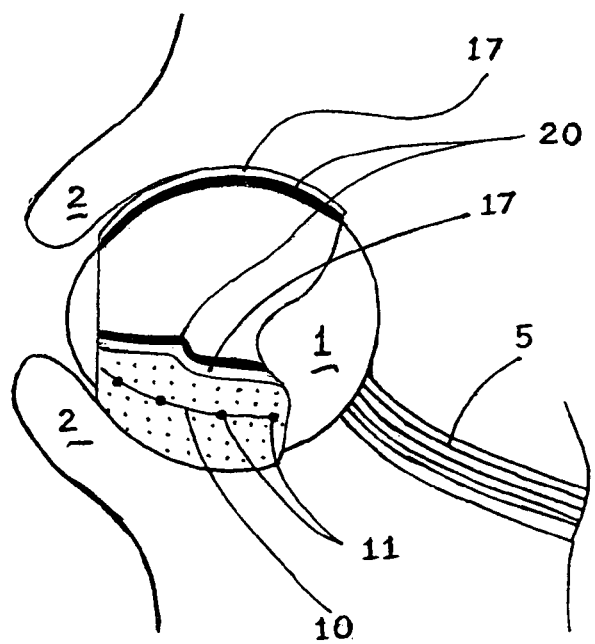
FIG. 10: Shows a side view of the plural layer shell with a more rigid structure such as ceramic insulation or lead shielding for its inner layer.

The plural cavity shell may contain a rigid outer layer or cavity 17 shown in FIG. 9 or a rigid inner layer or cavity 17 shown in FIG. 10. This rigid or semi-rigid layer or cavity not only maintains the structural shape of the device, but it can also serve as an insulator composed of a material such as ceramics or act as a shield comprised of a material such as lead covers and may provide other protective purposes. The system contains a plural cavity shell with a rigid material made of either ceramic, lead, steal, or other rigid substance, and it is located on its outer layer 19 or inner layer 20.

Figure 11:
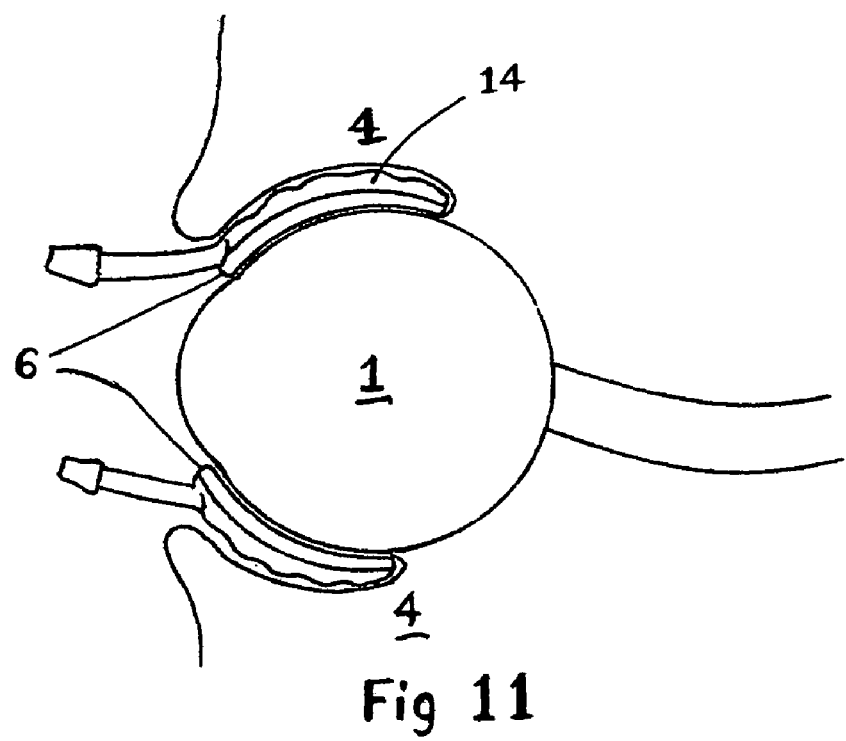
FIG. 11: Illustrates the shell with a soft pulsating outer shell wall creating a massaging mechanism for on its outer layer.
Figure 12:
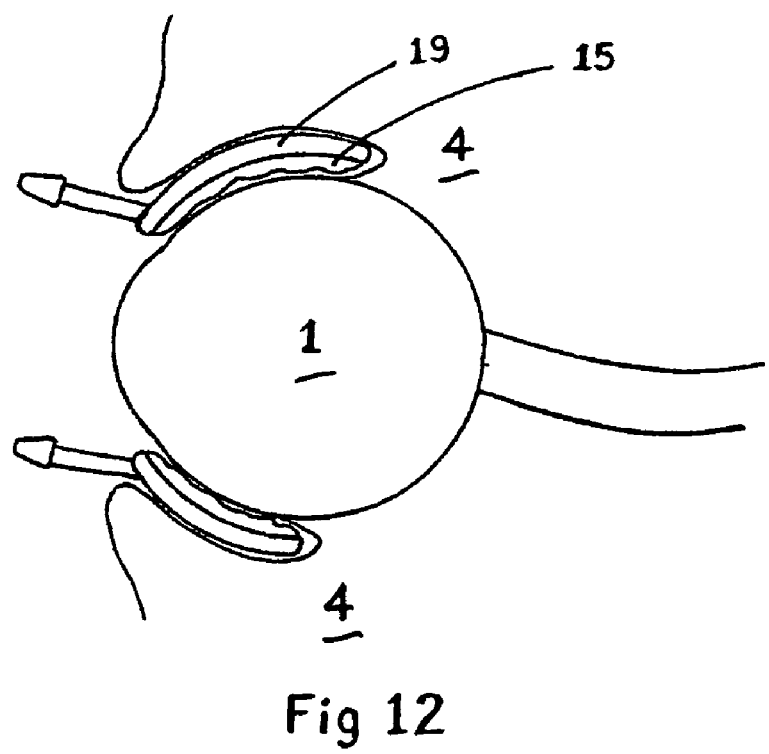
FIG. 12: Illustrates the shell with a soft pulsating inner shell wall creating a massaging mechanism on for its inner layer.

In another embodiment, the outer cavity 14 of the silicone rubber shell 6 in FIG. 11 is flexible and pulsating due to an attached pump mechanism that rhythmically raises and lowers the pump speed and pressure. This manually massages the orbital tissue to facilitate venous and fluid drainage to the cavernous sinus and prevents congestion of the orbit. This action may be useful in the treatment of acute ischemic optic neuropathy or in the prevention of ischemic optic neuropathy during prolonged back or neck surgery In another embodiment the firm outer shell layer or cavity 19 shown in FIG. 12 stabilizes the orbit while the inner pulsating shell layers 15 massage the eye 1 to lower the intra-ocular pressure and facilitate intra-ocular vascular flow.

As seen in FIG. 4 the cross-sectional view of the thermal-regulating shell 6 supports a posterior opening 12 suitable in size to allow the shell 6 to conform and slip over the eye 1.

Figure 13:
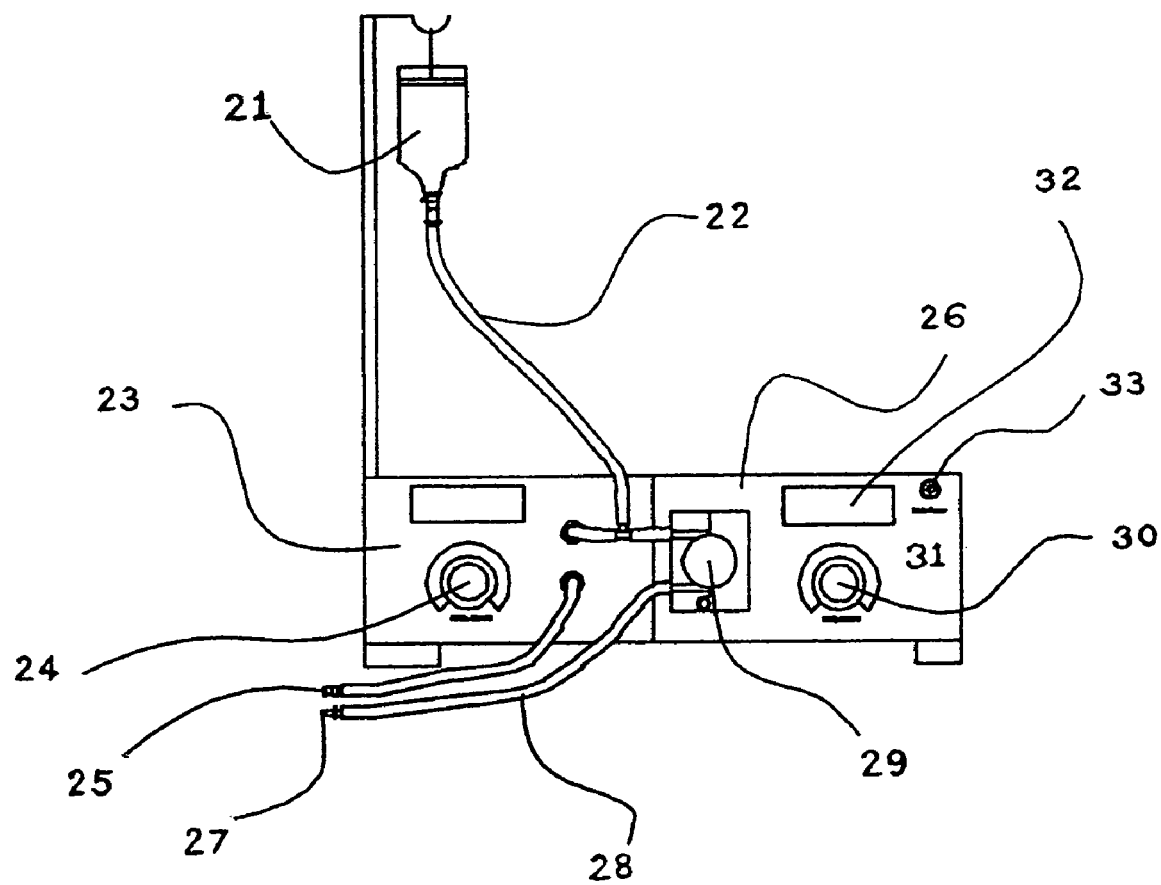
FIG. 13: Displays the apparatus for controlling fluid temperature, pressure, rate of flow, flow pulsation in order to circulate temperature controlled and pressure controlled fluid to and from the shell.
Figure 14:
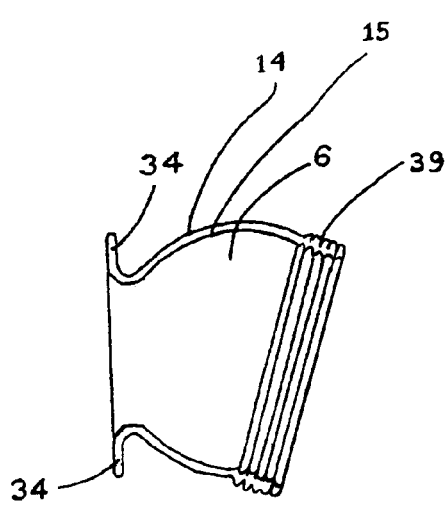
FIG. 14: Illustrates a thermal-regulating shell with an eyelid speculum incorporated therein and a compressed posterior shell extension.

As shown in FIG. 13 fluid temperature and fluid circulation can be controlled to predetermined temperatures and rates of fluid flow. Positive pressure is controlled by raising and lowering a fluid bottle 21 height. Fluid pressure is communicated through a fluid tube 22.

Fluid flow is then presented to a temperature control unit 23. Fluid temperature is adjusted to the desired setting by means of the temperature control selector 24. Temperature conditioned fluid is then provided to the supply connector 25 as seen in FIG. 13. Return fluid is presented to the fluid management unit 26 by means of the fluid return connector 27.

Using a suitable fluid path tube 28 fluid is pulled from the fluid return connector 27 by means of a fluid pump 29.

Fluid flow is controlled throughout the fluid management system 26 by adjusting the fluid pump speed. Speed selection is adjusted by means of a speed selector 30 which is displayed on the front panel 31 of the fluid management system 26 using a suitable pump speed indicator 32. The fluid management is preferably powered electrically with input power controlled by a suitable power switch 33.

Figure 15:
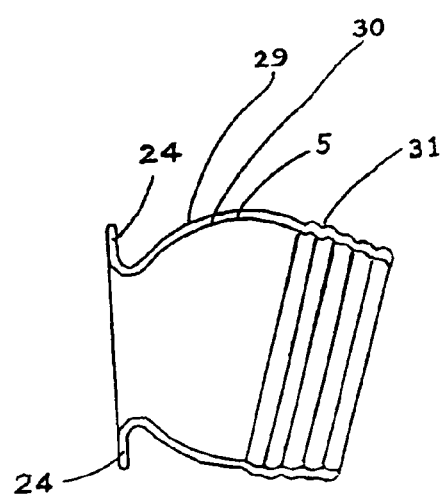
FIG. 15: Represents the thermal-regulating shell with the posterior extension extended by positive fluid pressure.
Figure 16:
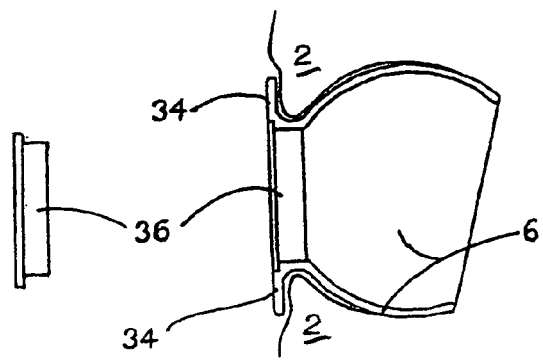
FIG. 16: Shows a side-view cross-section of the thermal-regulating shell with a built-in lid speculum in order to restrain the eyelids with and a means to fixate other diagnostic and treatment instruments over the eye.
Figure 17:
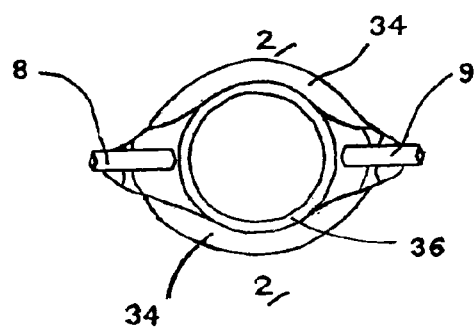
FIG. 17: Provides a front view of the thermal-regulating shell having the fluid ports entering and exiting the shell; with the lids held open by the built-in lid speculum placed superiorly and inferiorly, the shell being placed in the superior and inferior fornices around the eye.

Another means for retaining the thermal-regulating shell 6 is demonstrated using the eyelids 2 which fixate and conform to an eye speculum 34 as shown in FIGS. 6 and 7. The compressed posterior extension 35 is also shown in FIG. 6. The shell 6 conforms to the eye 1 and can be expanded posteriorly by unfolding its posterior extension 35, as shown in FIG. 15. The speculum 34 may be integrated into the thermal-regulating shell's geometry 6. The speculum 34 geometry may also incorporate suitable rigid or semi-rigid geometry to facilitate attachment of other instruments (not shown). As shown in FIGS. 16 and 17, a preferred counterbore fixation ring 36 may be incorporated into and around the speculum geometry 34.

Figure 18:
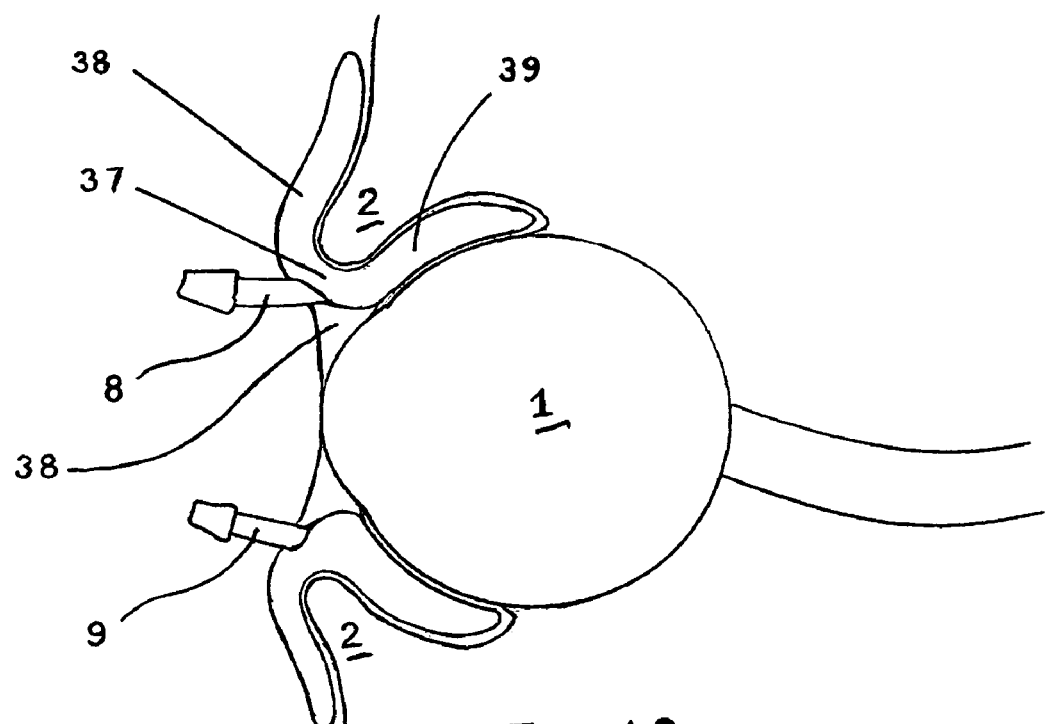
FIG. 18: Displays the side view of the thermal-regulating plural layer lid speculum where the part of the device is tucked under the eyelids with thermal-regulating shell-like posterior extension over the eye.

In a preferred embodiment, a thermal regulating device having the shape of a plural layer lid speculum 37 is shown in FIG. 18. Its anterior portion 38 cools the eyelids while its posterior portion 39 hooks under the lid to serve as a lid speculum 37 as well as a thermal-regulating apparatus for both the lid and the eye.

Figure 19:
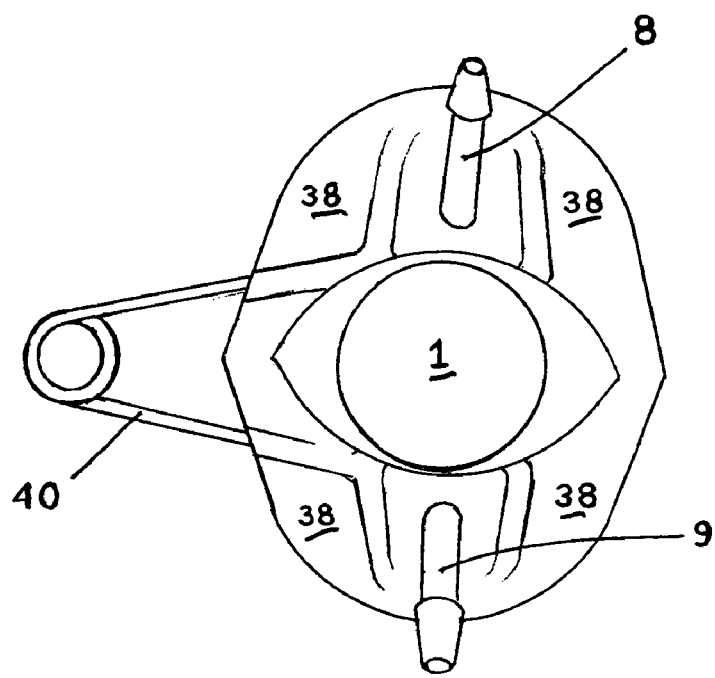
FIG. 19: Represents the frontal view of the thermal-regulating lid speculum with underlying posterior shell extension and an inserting clamp attached.
Figure 20:
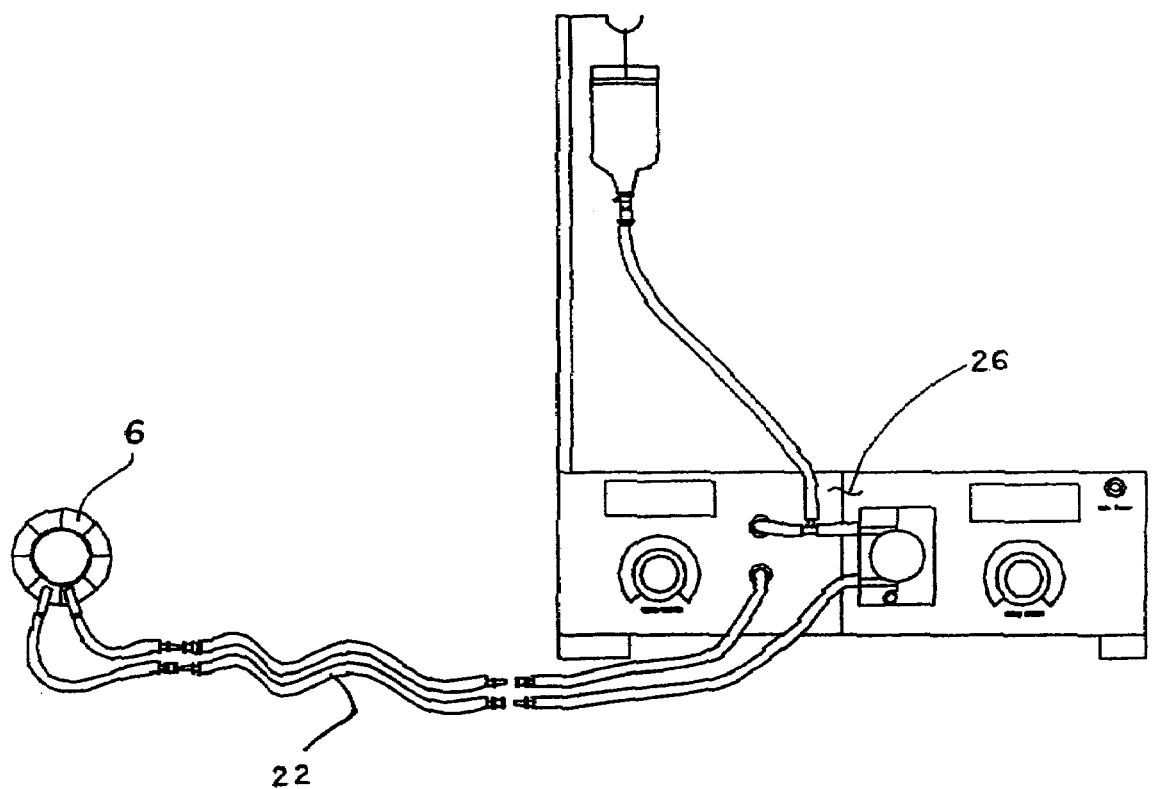
FIG. 20: Depicts a system configuration including a fluid management system, thermal-regulating shell and related fluid tubing.

FIG. 19 shows the frontal view of the thermal-regulating lid speculum with its anterior portion 38 visible and its posterior portion 39 functioning as a shell extension hidden from view and an inserting clamp 40 attached;

In FIG. 20 the fluid management system 26 is communicated to the thermal-regulating shell 6 by means of suitable fluid tubing 22.

Figure 21:
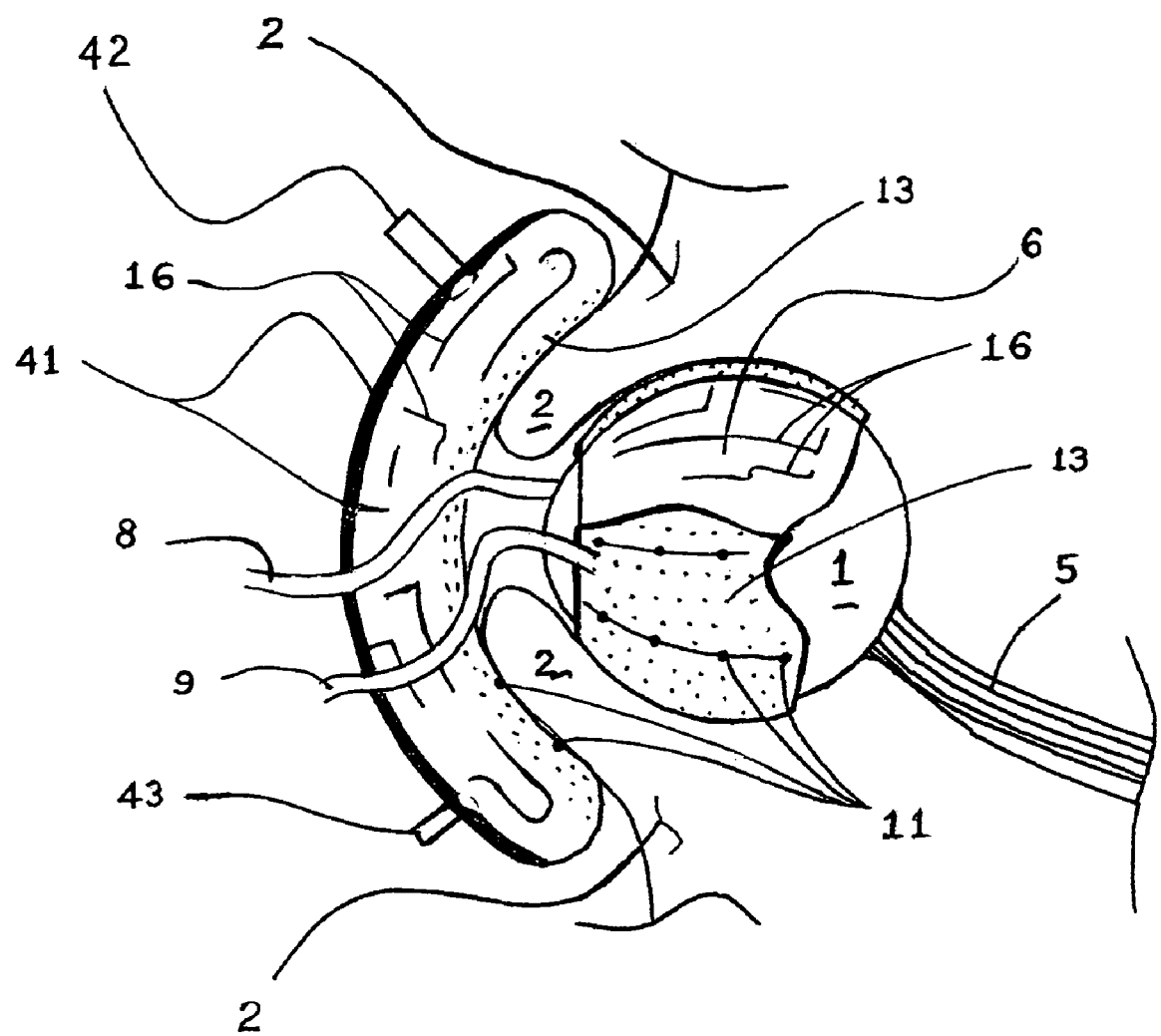
FIG. 21: Provides a cross section view of the eye having the thermal-regulating shell installed over the surface of the eye, with a cooling patch disposed over fronts of the partially closed eyelids, each device commanding its own thermal-regulating pump system.
Figure 22:
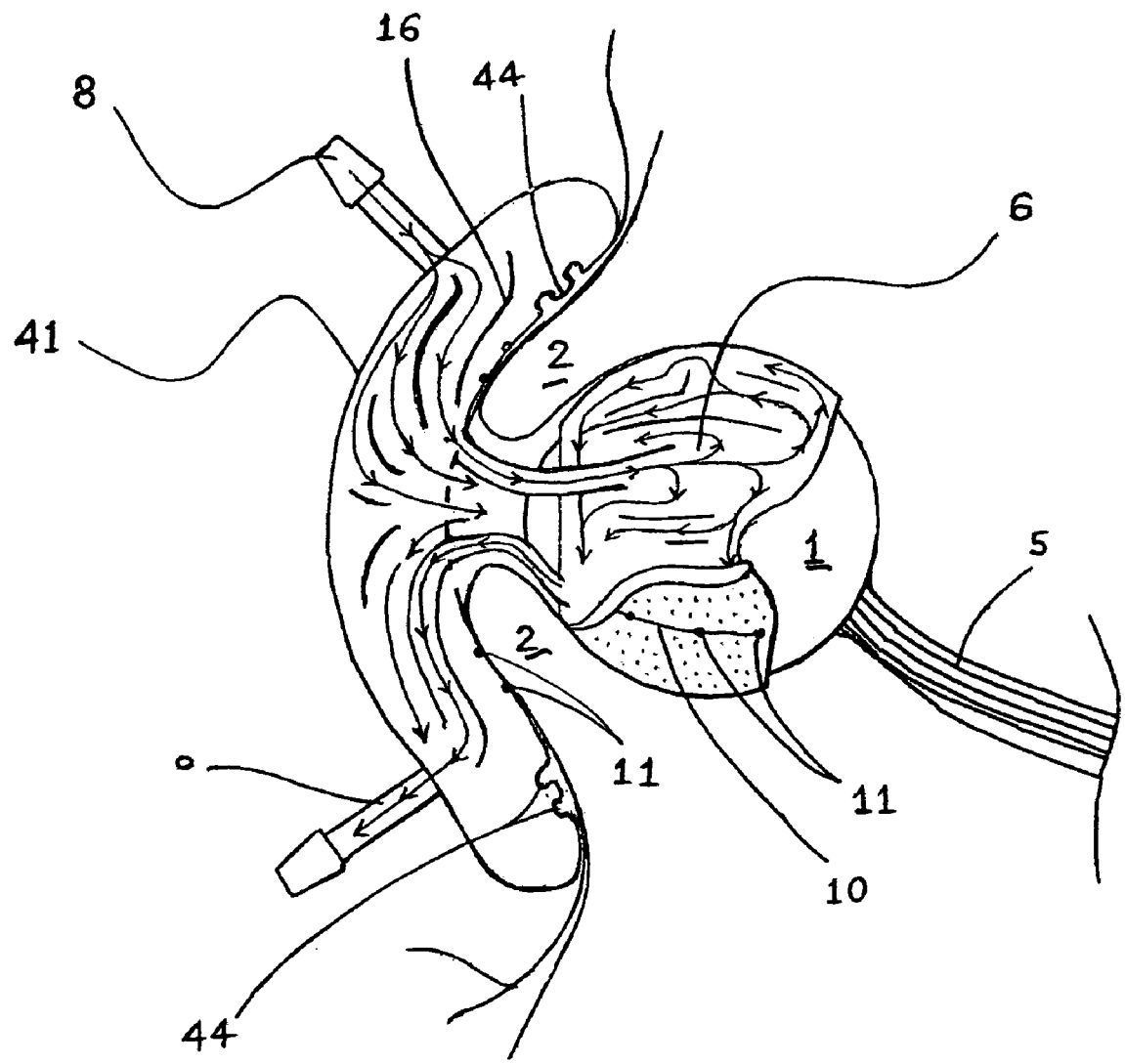
FIG. 22: Depicts the cross section view of the eye with an integrated zip-lock system of the patch with the shell sharing the thermal-regulating fluid and patch.

Another means of maintaining thermal-regulating shell 6 placement as well as additional eye cooling can be achieve through the use of a cooling patch 41 with flow channels 16 and separated from the thermal-regulating shell 6 as shown in FIG. 21 or combined with the shell as shown in FIG. 22. Channels 16 are used to encourage fluid flow to the posterior shell in the combined unit.

Figure 23:
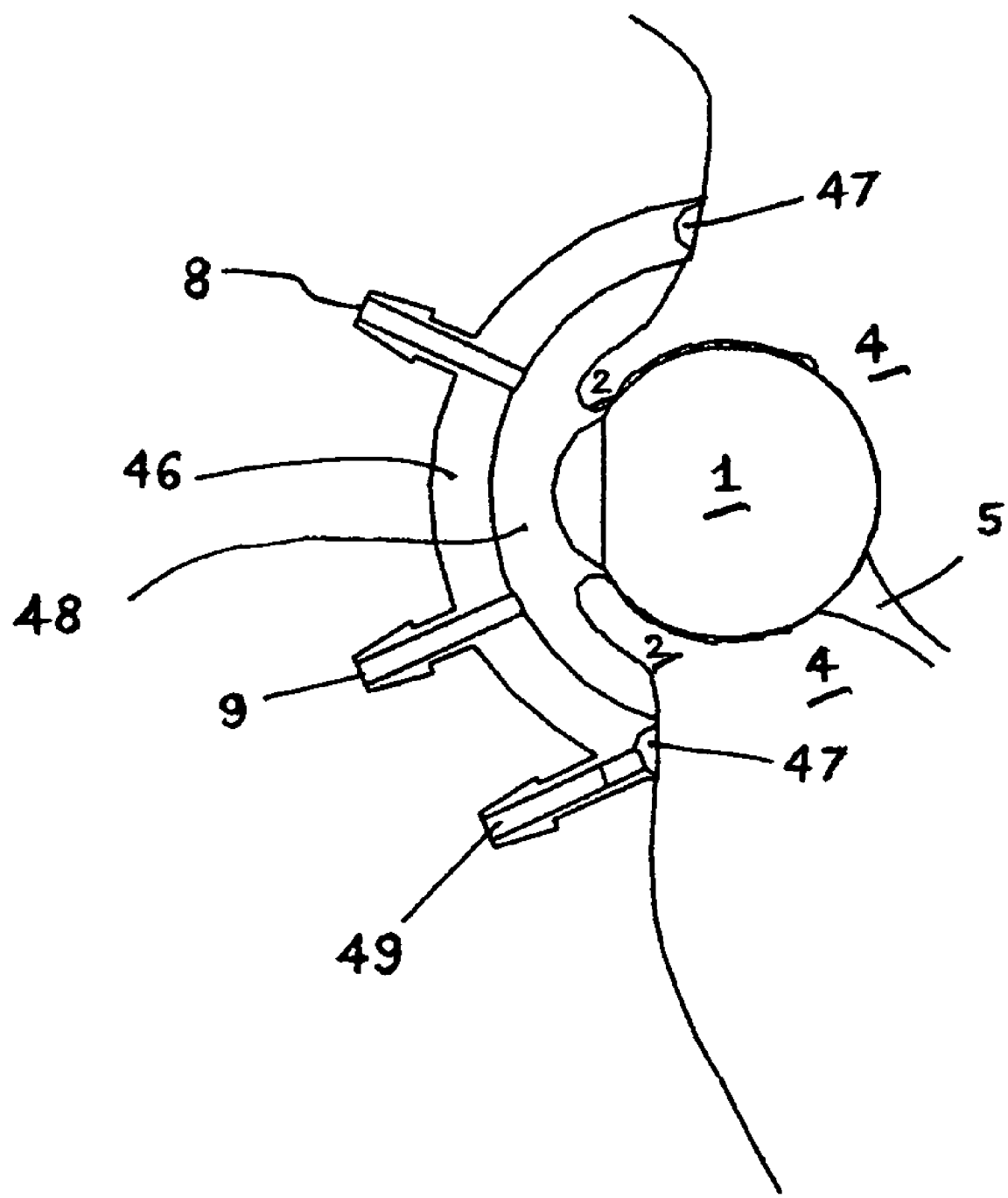
FIG. 23: Displays a side view of a suction-aided system for the thermal regulation of the eye, eyelid and peri-orbita.

Another means of maintaining thermal-regulation is the use of the suction aided system 46 that cools the eyelids 2, eye 1, and anterior orbit 4 as shown in FIG. 23.

Method of Operation

Thermal-regulation of the eye 1 and the surrounding tissues can be used for various therapeutic and interventional purposes. The thermal regulating device 6 uses both conductive and convective methods for temperature control of the eye 1, and the surrounding tissue.

The device 6 may include an anterior central opening 7 to allow for direct inspection of the cornea and other ocular structures when the device 6 is installed on the eye 1. Alternatively, the shell 6 may have no central opening and in this embodiment the cornea, the anterior segment, the eye and nearby tissues can be even more effectively cooled.

Fluid entry ports 8 and fluid exit ports 9 may be placed anywhere on said device 6 though preferentially medially or laterally to take advantage of anatomical relationship of the eye 1 and eyelid 2. There will be a thermal exchange of temperature using conduction between the shell 6 and the eye 1 or other nearby structures and convection of the rapidly moving irrigating fluid.

This device 6 is composed of a material that facilitates heat exchange between the eye 1 and the conductive fluid. A material such as silicone rubber or any other material with properties such as softness, malleability, and good heat-exchange capability is desired.

For purposes of administration of medications and other chemicals, the material may consist of a semi-permeable membrane, or millipore/micropore systems, or microtubules 13, or nanotubules, or material that has been prepared with special channels 16 in its cavities 17 for passage of treatment modalities.

The body of the shell 6 may be reinforced with a wire 10 or other firm mesh resulting in a supporting matrix 10. Various sensors 11 may be embedded in the wire matrix 10 or in the shell 6 in order to take readings throughout the involved tissue surfaces. The embedded sensors 11 can measure various ocular surface properties such as ocular temperature, ocular pressure, ocular surface pH, ionic concentrations, chemicals detection or concentrations, oxygen saturation, drug concentrations, and other monitoring features yet to be in common use.

The matrix 10 firmness also assists in pushing the fornices 3 posteriorly and extending the shell 6 coverage to the posterior surface of the eye 1 as shown in FIG. 15. In treatment for the posterior globe or orbit 4, it may be necessary to surgically incise the posterior wall of the fornix 3 to allow the shell 6 to extend more posteriorly. This may require the use of an inserter (not shown) to give direction and placement into the posterior orbit and near the back of the eye 1.

Referring to FIG. 4, the device 6 is a dual or plural layer system enclosing one or more cavities 17 within which circulates the fluids for heat exchange. Within these cavities there will be ridges 18 and channels 16 that redirect the circulating fluids to maximize heat-exchange. Thermal-regulation of the posterior portion of the eye 1 will be optimized via these channels 16 which may contain one-way valves and gates to redirect fluids. These features will allow for rapid as well as even or uneven distribution of fluids.

In another preferred embodiment, these channels 16, gates, or shell layers may have micropores/millipores 13 of various dimensions to allow selective filtration or passage of molecules of certain sizes.

In another embodiment, the outer coated layer 19 of the silicone rubber shell 6 can be coated with ceramic, lead, or another insulating material to maximize thermal regulation of the eye 1. For other purposes, the inner coated layer 20 or part thereof may be coated with ceramic, lead, or other insulating material to protect the eye or other structures from temperature changes when treating tissue outside of the eye 1.

In another preferred embodiment, the shell 6 can have an expandable posterior extension 35 that expands and pushes the fornices 3 posteriorly. This expansion can be achieved by positive pressure from the fluid circulating throughout the cavity or more directly from additional fluid inlet ports. Although the device is non-invasive, it can push the flexible and yielding ocular fornices 3 beyond the normal anatomical end-points effectively cooling the posterior retina, macula, vitreous, optic nerve 5, orbit, adnexae and other surrounding tissues.

If an incision of the posterior fornix is done, there will be extension of treatment beyond the conjunctiva and fornices 3 and a greater surface area can be treated by the device 6.

The dual or plural layered system can provide both positive and negative pressure on the eye 1 by either pulsing or keeping a constant pressure. Eye-pressure measuring devices 11 can be incorporated into the encapsulating shell device 6 to monitor the intraocular pressure and regulate the fluids flowing through the device 6 to prevent excessive pressure on the eye 1.

Other embodiments of the shell design 6 include an integrated cooling system for the eye 1 and eyelid FIG. 6. The eyelid 2 may be cooled mainly by lid speculum 34 by holding the eyelid 2 apart. The thermally controlled fluid in this extension can be integrated with the rest of the shell's temperature-controlled system.

Alternatively, in another preferred embodiment, the eyelid temperature-controlled system and the eye globe temperature-controlled system can be regulated separately by separate fluid pump systems to maximize the inner 20 and outer 19 shell's thermal-regulating effects to create differential cooling in different volumes of the eye and periorbital tissues.

In addition, separate temperature controls of two or more compartments within the shell 6 can create a temperature gradient if it is so desired. The temperature gradients can then influence the flow characteristics of fluids within the eye 1.

In another preferred embodiment of the device 6, the outer layer lid-speculum system 37 may be a separate unit with its own temperature-regulating system for the eyelids and nearby structures and doubly serves as an eyelid speculum 34. This system works in conjunction with a shell device 6 for the eye 1 to temperature regulate the eye 1 and the lid separately. This or another embodiment may use a clamp 40 for easy insertion and retraction of the device. This system in conjunction with a central opening 7 for the shell 6 allows the eye 1 to be exposed for therapeutic observation or intervention and treatment.

In another preferred embodiment, if the eye 1 is covered by a shell without a central opening and does not need to be exposed, the eye will have more efficient temperature control due to a greater surface area being treated. An outer thermal-regulating heat exchange pad 41 with channels 16 can cover the closed eyelid 2. A separate system for entry 42 and exit 43 ports are needed for this pad 41. However, an alternative integrated system 45 will incorporate both the pad 41 and shell 6. To secure this pad 41 a zip-lock system 44 may be used.

This outer device 41 may be loosely or firmly placed on or near the eyelid 2 as a pad or patch with the help of adhesives, suction mechanisms or other mechanical means. Within the cavities 17 there will be ridges 18 and channels 16 that redirect the circulating fluids to maximize heat-exchange.

Alternatively, in another preferred embodiment, a conductive heat-exchange system 46 can encapsulate the eyelid 2 forming a complete sealed system with the use of a vacuum chamber 47 whereby fluid 48 can freely circulate directly around the eye 1 for the purpose of cooling, heating, drug-delivery, irrigating, and other functions. The sealing can be accomplished with a zip-lock system 44, a suction-aided system 46, a mechanical clamp 40 or other mechanical means to form a cavity bordered by said device anteriorly and the eye posteriorly. The suction system 46 is accomplished by removing air via the vacuum port 49 by creating a vacuum in the vacuum chamber 47.

An anesthetic solution and/or gel can be applied to the eye 1 to prepare for the insertion of the device 6. The anesthetic material may be coated on the shell 6 prior to insertion beneath the lids 2. Commercially available anesthetic solutions such as Proparacaine or Tetracaine and anesthetic gels such as Lidocaine are readily available.

The eyelid 2, ocular surface and surrounding areas are then properly cleansed with antiseptic solutions such as Betadine and properly covered with a sterile drape. Other techniques are available and can be chosen according to the desired level of topical and local anesthesia.

For example, peri-bulbar or retro-bulbar injection of Lidocaine and Bupivacaine can achieve very deep and complete local anesthetic effects. Alternatively, a Tenon's infiltration of local anesthetics with a blunt Greenbaum cannula has essentially no risk of globe perforation yet quite effectively renders deep local anesthesia. In addition, an anesthetic lid block may be desirable in certain situations to facilitate eyelid speculum 34 and device 6 insertion and maintenance.

With the eyelid 2 manually separated, the device 6 is inserted into the cavity surrounding the globe. The shape of the device 6 takes advantage of the different posterior depths of the fornices 3 in different quadrants to maximize its reach. Depending upon its use, the device 6 can be prefabricated to have a less protracting depth. The device 6 can reach deeper in this sequence: medially, inferiorly, superiorly and laterally.

Medially, the medial canthal tendons tend to limit the posterior reach while temporally and superiorly, the extensions of the fornices are quite posterior. In one technique, the eyelids 2 are allowed to stay closed throughout the procedure. Alternatively, a standard lid speculum or a thermal-regulating device shaped similarly to a speculum 34 is inserted to keep the eyelid 2 apart followed by insertion of the thermal-regulating shell 6.

Further, the combined thermal regulating-eyelid speculum devices 34 as shown in FIG. 14 through 19 may be used to keep the eyelid 2 apart. FIGS. 16 and 17 show the same device as FIG. 14 with the addition of a ring base 36 or other suitable rigid or semi-rigid geometry that can support various diagnostic or surgical devices including but not limited to a gonioscope, viewing prisms, fundus contact lenses, medication wells, and others.

Although there has been hereinabove described a specific medical device and method for temperature control and treatment of the eye and surrounding tissues in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method of preventing neurological damage, ocular damage and orbital damage to an eye, said method comprising:
   inserting a shell over an external surface of the eye within superior and inferior fornices beneath the eyelids;
   controlling a temperature of the eye and orbit by circulating fluid within the shell; and
   inspecting a cornea and other ocular structure through a central opening when the shell is inserted over the eye.

2. The method according to claim 1 further comprising measuring ocular properties by way of sensors disposed in the shell.

3. The method according to claim 1 further comprising controlling a pressure of the circulating fluid.

4. The method according to claim 1 further comprising massaging the eye by regulating a pressure of the circulating fluid.

5. The method according to claim 4 wherein massaging the eye includes disposing a pulsating unit between the shell and the eye in order to raise and lower intra-ocular pressure.

6. The method according to claim 4 further comprising causing passage of emboli from a central retinal arteries to a more peripheral location by massage.

7. The method according to claim 1 further comprising surgically increasing a posterior wall of the fornices before insertion of the shell.

8. The method according to claim 1 further comprises introducing a medicament into the eye through said shell.

9. The method according to claim 1 wherein inserting said shell and controlling eye temperature is performed before subsequent and separate eye surgery.

10. The method according to claim 1 further comprising performing eye surgery before insertion of said shell and controlling eye temperature.

11. The method according to claim 1 further comprises cooling of eyelids by way of a heat exchange pad.

12. A medical device for temperature control and treatment of an eye and surrounding tissue, said medical device comprising:
a shell sized and shaped to conform and slip over an eye, said shell having a posterior opening for enabling positioning of said shell over said eye;
a fluid entry port and a fluid exit port, both in fluid communication with said shell, for circulating fluid through said shell; and wherein said shell further comprises a central anterior opening for enabling inspection of the eye when the shell is disposed therein.

13. The device according to claim 12 further comprises sensors disposed in said shell for measuring ocular properties.

14. The device according to claim 12 further comprises apparatus for controlling fluid temperature, pressure, and rate of fluid flow through said shell.

15. The device according to claim 12 further comprising apparatus for varying pressure of fluid through said shell in order to massage the eye.

16. The device according to claim 15 wherein the apparatus for varying pressure includes a pulsating unit disposed between the shell and orbital tissues of the eye.

17. The device according to claim 12 wherein said shell further comprises means for introducing a medicament into the eye and/or priorbital tissue.

18. The device according to claim 12 further comprises an outer shell coating.

19. The device according to claim 18 wherein said outer shell coating is selected from a group consisting of an insulating material and a medicament.

20. The device according to claim 12 further comprises an inner shell coating.

21. The device according to claim 20 wherein said inner shell coating is selected from a group consisting of a thermal conducting material and a medicament.

22. The device according to claim 12 further comprising a speculum for separation and cooling of eyelids.

23. The device according to claim 22 further comprising a counter-bore fixation ring for facilitating attachment of other instruments.

24. The device according to claim 12 further comprising a cooling patch having fluid channels in fluid communication with said shell for cooling eyelids.

* * * * *